(12) United States Patent
Souard

(10) Patent No.: US 8,091,729 B2
(45) Date of Patent: Jan. 10, 2012

(54) PEELABLE STERILIZATION PACK

(75) Inventor: Sylvere Souard, Conches-sur-Gondoire (FR)

(73) Assignee: Amcor Flexibles SPS, Coulommiers (FR)

( * ) Notice: Subject to any disclaimer, the term of this patent is extended or adjusted under 35 U.S.C. 154(b) by 451 days.

(21) Appl. No.: 12/296,246

(22) PCT Filed: Apr. 6, 2007

(86) PCT No.: PCT/FR2007/000590
§ 371 (c)(1),
(2), (4) Date: Oct. 6, 2008

(87) PCT Pub. No.: WO2007/116139
PCT Pub. Date: Oct. 18, 2007

(65) Prior Publication Data
US 2009/0114654 A1    May 7, 2009

(30) Foreign Application Priority Data
Apr. 6, 2006  (FR) ..................... 06 03054

(51) Int. Cl.
| B65D 8/04 | (2006.01) |
| B65D 65/26 | (2006.01) |
| B65B 55/02 | (2006.01) |
| A61L 2/00 | (2006.01) |
| A61L 2/04 | (2006.01) |

(52) U.S. Cl. ............ 220/612; 220/359.4; 422/1; 422/26; 206/438; 206/484; 206/484.1; 383/210; 383/211; 53/425

(58) Field of Classification Search ............... 220/359.1, 220/359.4, 612; 215/232; 422/1, 26; 206/438, 206/439, 484, 484.1; 156/60; 383/210, 211; 53/425
See application file for complete search history.

(56) References Cited

U.S. PATENT DOCUMENTS

| 3,326,450 A | 6/1967 | Langdon |
| 5,635,134 A * | 6/1997 | Bourne et al. .................. 422/26 |
| 2005/0008527 A1* | 1/2005 | Bayer et al. ........................ 422/1 |
| 2005/0079093 A1* | 4/2005 | Cannady et al. .................. 422/1 |
| 2005/0201812 A1* | 9/2005 | Wong et al. ....................... 401/7 |

FOREIGN PATENT DOCUMENTS

| DE | 20113173 | 10/2001 |
| GB | 988693 | 4/1965 |
| WO | 9845115 | 10/1998 |

OTHER PUBLICATIONS

International search report in corresponding PCT/FR2007/000590.
European Office Action, Dated Apr. 16, 2010, in Application No. 07731263.5.

* cited by examiner

*Primary Examiner* — Anthony Stashick
*Assistant Examiner* — Madison L Wright
(74) *Attorney, Agent, or Firm* — Young & Thompson

(57) ABSTRACT

The invention concerns a peel-off package for sterilization.

18 Claims, 5 Drawing Sheets

PEELABLE STERILIZATION PACK

FIELD OF THE INVENTION

The invention relates to a peelable sterilization pack.

BACKGROUND OF THE INVENTION

Sterility is a transient condition. The sterility of an object can only be understood in relation to the protection of this condition. Packaging is a vital step in the process of obtaining a sterile condition. Packaging means are designed to resist the usual stresses of sterilization, transport and storage in order to allow easy handling and opening.

Several techniques exist for sterilizing medical devices and in particular instruments intended to be in contact with the human body, in particular surgical instruments. Among these techniques there can be mentioned the most commonly used techniques, which are ethylene oxide sterilization, steam sterilization and gas plasma sterilization.

During the sterilization process, the item to be sterilized or the tray of instruments containing the items to be sterilized are first wrapped in a material one of the functions of which is to maintain the sterility of the product once the sterilization stage is complete. This material must prevent any subsequent contamination without reducing the effectiveness of the sterilization stage. The choice of the material is thus dictated by the constraints specific to each sterilization technique.

Two techniques are commonly used in the medical field for wrapping the items to be sterilized or the trays of instruments containing the items to be sterilized.

The first involves wrapping the object to be sterilized with a material suited to the sterilization process by adopting the "Pasteur" folding technique. According to this technique, no sealing is carried out to close the pack, a repeated folding of the material makes it possible to obtain a tortuosity sufficient to maintain the sterility of the pack contents. This technique is particularly suitable for the sterilization of bulky and/or heavy objects. However if the folding is of poor quality, the sterility of the object will not be maintained over time. The maintenance of sterility depends on the quality of the folding. This technique therefore has the disadvantage of depending very largely on human intervention.

The second technique involves placing the object to be sterilized in a peelable pack. Once the object is in the pack, the pack is sealed, then subjected to the sterilization stage. The packs are most often constituted by two separate sheets constituted by different materials. One of the sheets is most often transparent. The packs are suited to the sterilization technique used. The peelable packs being constituted by two heat-sealed sheets, the mechanical strength can be limited by the mechanical strength of the weld which produces the seam between the two sheets, or by the strength of the pack itself.

One of the purposes of an embodiment of the present invention is to provide a peelable sterilization pack which is suitable for bulky and/or heavy objects in order so far as possible to minimize human intervention, and thus the risks of subsequent contamination.

SUMMARY OF THE INVENTION

An embodiment of the present invention is a support suited to at least one sterilization method and to sterility maintenance, comprising on one of its faces a heat-sealable adhesive, said adhesive forming a strip which describes a curve, said curve being symmetrical with respect to an axis, said axis being the axis of folding of the support, said support once folded and heat-sealed being able to constitute a peelable sterilization pack, characterized in that the support is constituted by a material constituted by a polymer or a mixture of polymers chosen from the group constituted by high-density polyethylene, polypropylene, polyamide and polyester.

According to another embodiment of the invention, the invention relates to a support suited to at least one sterilization method and to sterility maintenance, comprising on one of its faces a heat-sealable adhesive, said adhesive forming two strips which describe two curves, said curves being symmetrical to each other with respect to an axis, said axis being the axis of folding of the support, said support once folded, trimmed and heat-sealed being able to constitute a peelable sterilization pack, characterized in that the support is constituted by a material constituted by a polymer or a mixture of polymers chosen from the group constituted by high density polyethylene, polypropylene, polyamide and polyester.

DETAILED DESCRIPTION OF THE INVENTION

Figure 1:
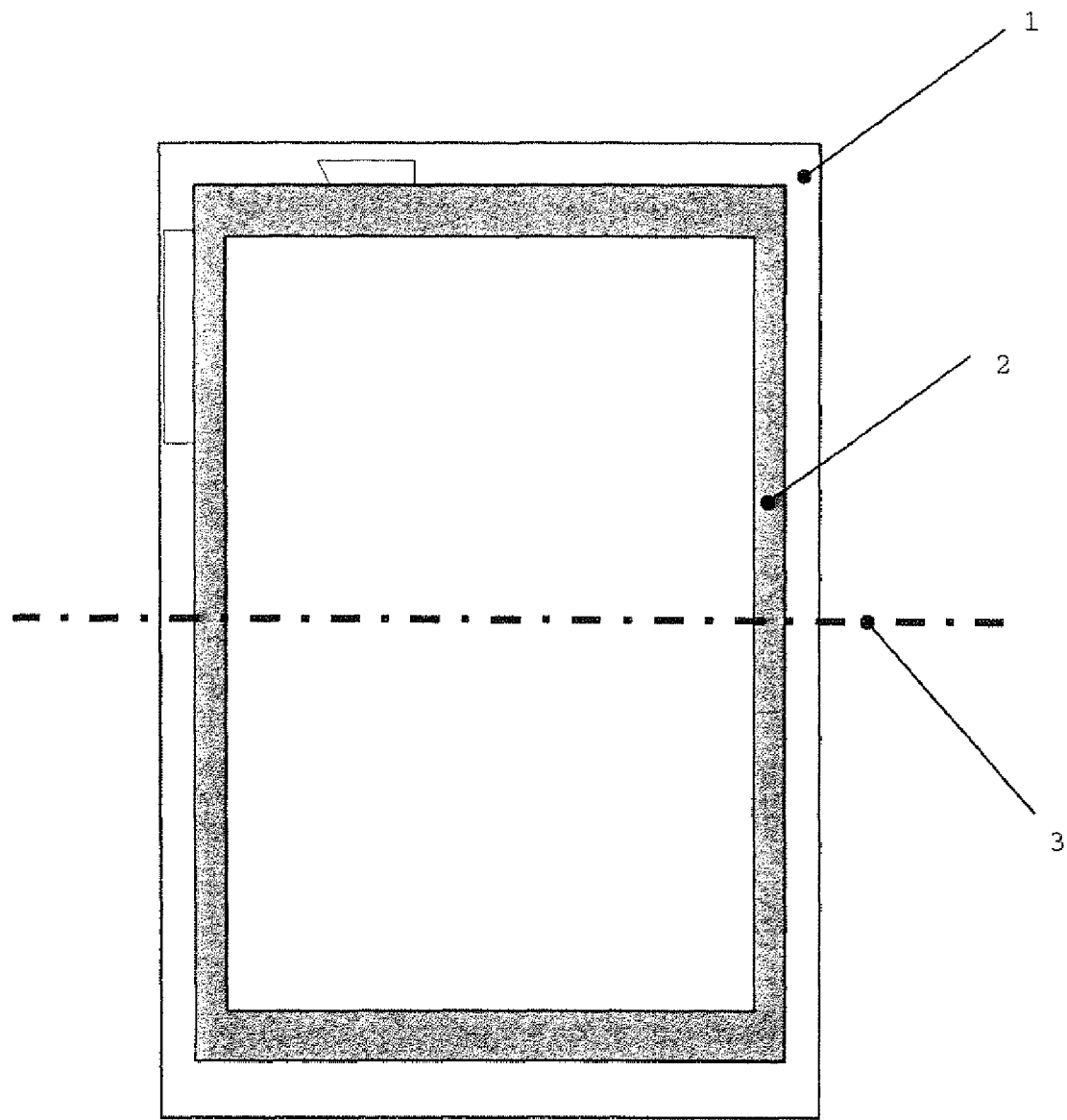
FIG. 1 schematically represents an embodiment of the invention. It is a view from above of the support (1) to which a strip of heat-sealable adhesive (2) has been applied. The axis of folding and of symmetry (3) is represented as a dotted line.

By pack is meant anything which is used for wrapping, this may be for example a sack, bag, pouch or pocket.

By peelable pack is meant a pack which is capable of being opened at the heat-sealed seam as a result of a force exerted by the user. Typically, opening will be achieved by breaking the adhesive-adhesive bond.

Typically, said curve or curve(s) is (are) closed or not closed. When said curve(s) is (are) not closed, the tightness of the packaging will be ensured by heat-sealing the support directly onto itself. To do this, a person skilled in the art will choose supports constituted by materials which allow the support to be heat-sealed onto itself. Such materials are for example SMS and SMMS.

Typically, the surface area defined by the curve or curves can be variable and will be in relation to the size of the items that are to be sterilized. Typically, the area can be comprised between 100 cm$^2$ and 20,000 cm$^2$, in particular between 1000 and 10,000 cm$^2$.

The support is constituted by a material which makes it possible to maintain the sterility of the product once the sterilization stage is complete. This material prevents any subsequent contamination without reducing the effectiveness of the sterilization stage. The material has a sufficient permeability to all the physical and/or chemical agents affecting the efficiency of the sterilization process. Moreover, the material allows the evacuation of these agents after the sterilization.

Typically, the support is constituted by a material suited to at least one sterilization method chosen from steam sterilization, ethylene oxide sterilization and gas-plasma sterilization.

According to a particular embodiment, the support is constituted by a material suited to at least two sterilization methods chosen from steam sterilization, ethylene oxide sterilization and gas-plasma sterilization. The use of such materials makes it possible to obtain a "universal" peelable pack, i.e. suited to the main sterilization techniques.

According to a preferred embodiment, the support is constituted by a material suited to steam sterilization.

Preferably the material is nonwoven. Typically the material has an SMS (spunbond-meltblown-spunbond) or SMMS (spunbond-meltblown-meltblown-spunbond) type structure. Alternatively the material is of Tyvek® or Dextex® type. All these materials are known to be suited to the sterilization of medical and surgical equipment.

The heat-sealable adhesive used for the present invention advantageously has an adhesive-adhesive bond which is weaker than the adhesive-support bond so as to minimize the release of fibres during the opening of the pack.

According to a particular embodiment, the adhesive is a water-based adhesive.

By way of example of water-based adhesives which a person skilled in the art can use, there can be mentioned: hydrocarbon and styrenic resins, vinylic emulsions, ethylene copolymer dispersions and waxes.

Typically, the heat-sealable adhesive can be applied to the support at ambient temperature.

Advantageously, in order to reduce any problem of permeability caused by the use of water-based adhesive, the adhesive can be applied to a area of the support coated with a hydrophobic agent. By way of example of a hydrophobic agent, thermoplastic hydrocarbon resins can be mentioned. The coated area can cover an entire face of the support or cover only a strip of the support.

Figure 2:
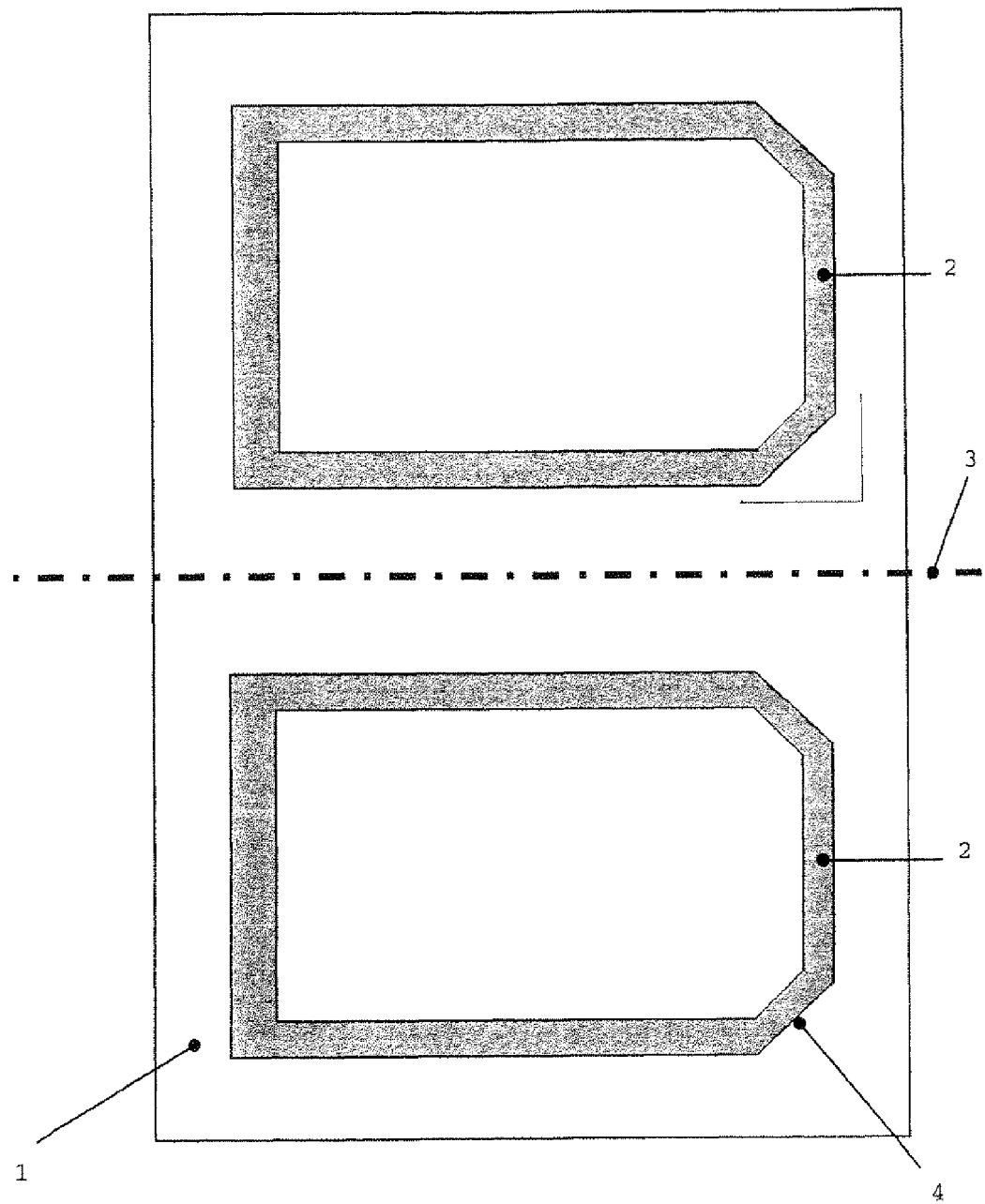
FIG. 2 schematically represents another embodiment of the invention. It is a view from above of the support (1) onto which two strips of heat-sealable adhesive (2 and 2') have been applied. The axis of folding and of symmetry (3) is represented as a dotted line. Two peelable tabs (4) are represented.
Figure 3:
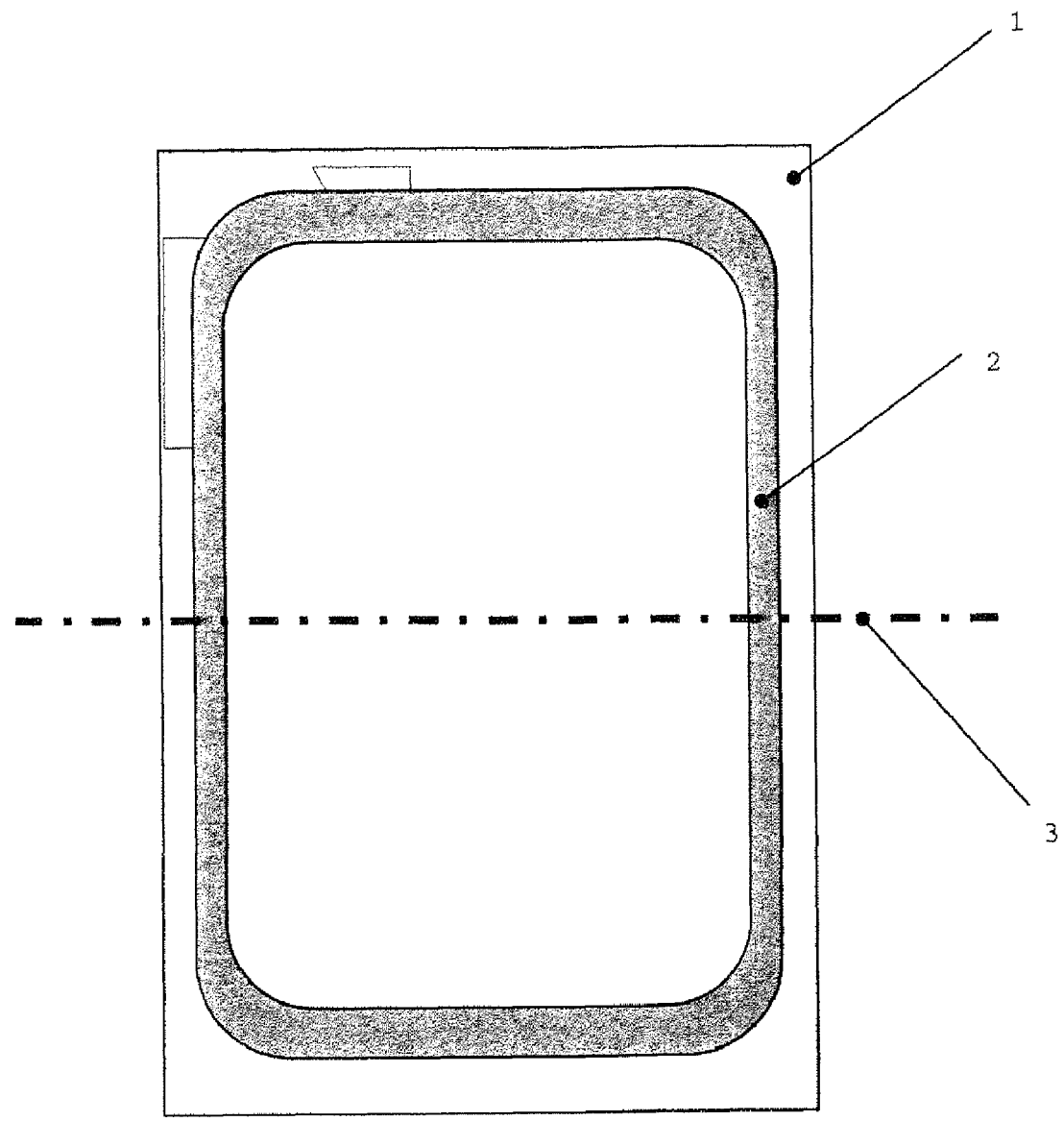
FIG. 3 schematically represents an embodiment in which the peelable tabs (4) have a rounded shape.
Figure 4:
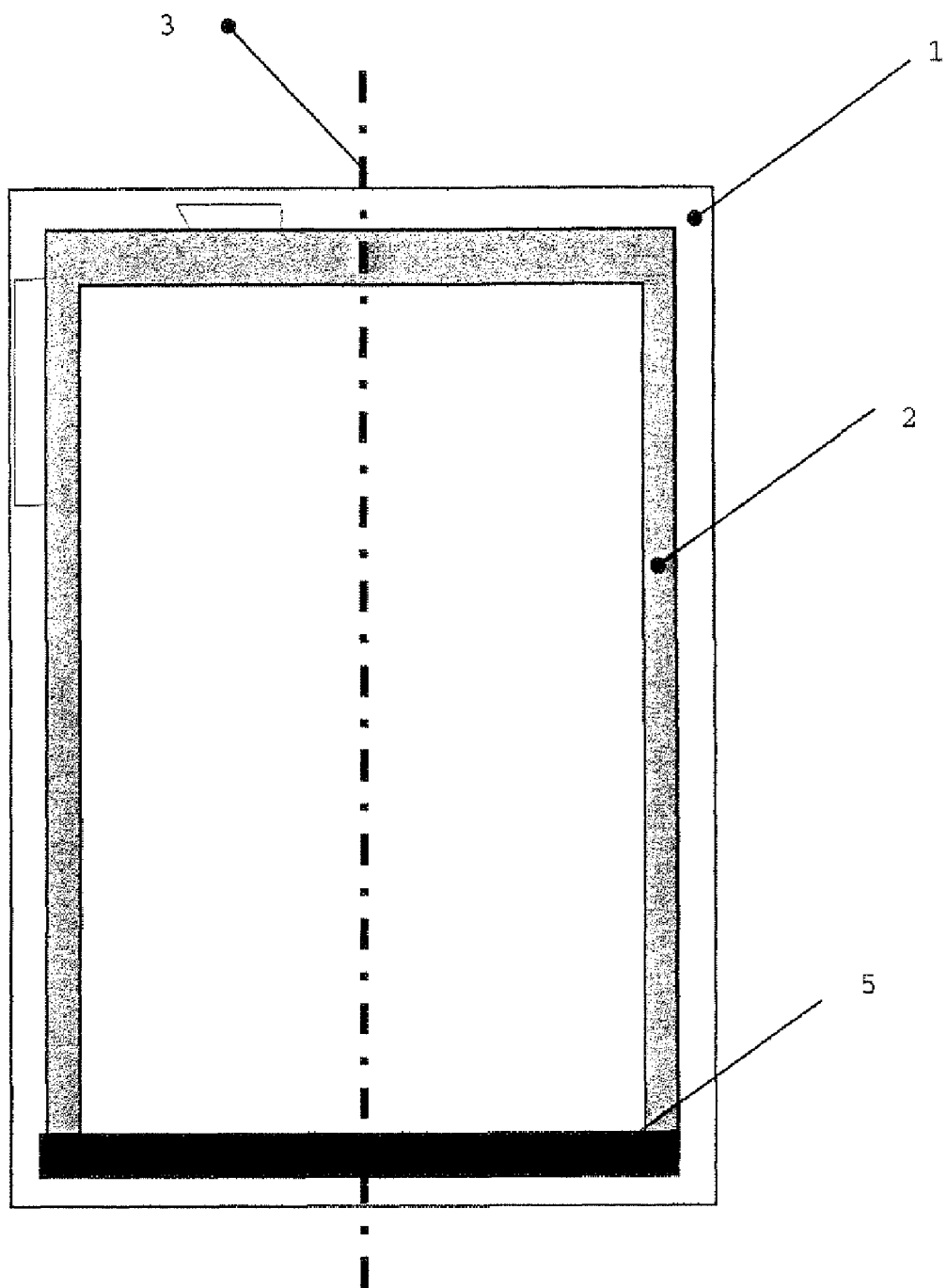
FIG. 4 schematically represents an embodiment of the invention. The area (5) of the support corresponds to the area of the support which will be heat-sealed onto itself.
Figure 5:
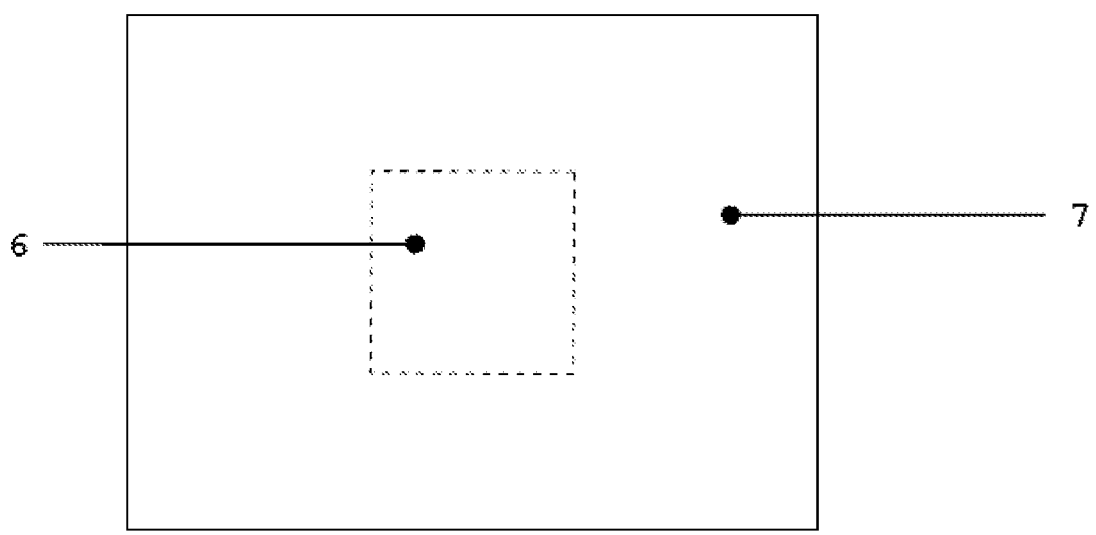
FIG. 5 schematically represents an embodiment of the invention in which a set of peelable packs comprises a first peelable pack (6) contained in a second pack (7), both packs being suited to the same sterilization method.

According to a particular embodiment, the closed curve has an essentially rectangular shape. Typically, in order to facilitate opening of the pack by the user, the rectangular shape can be modified so as to provide one or more peelable tabs. For example, one or two angles of the rectangular shape may be truncated (cf. FIG. 2). Advantageously, the rectangular shape can have rounded corners in order best to distribute any mechanical stresses induced by the contents of the pack on the sealed seam.

The heat-sealable adhesive can be applied in a strip following the curve or curves as described above on the support according to all the usual techniques, for example application to a area according to a heliographic, planographic or flexographic process.

Typically the width of the adhesive strip applied onto the support can vary along the curve. Typically, it can be provided that for the part of the adhesive strip which will be heat-sealed by the final user, the width of the strip will be 1.2 to 3 times wider than the maximum width of the strip over the remainder of the curve. Thus sealing by the final user of the pack is facilitated.

According to the mechanical strength desired after sterilization for the weld which ensures the closing of the pack, a person skilled in the art will choose a heat-sealable adhesive suited to the sterilization method and will vary the width of the adhesive strip and the quantity of adhesive applied onto the support. Typically the mechanical strength of the weld will be comprised between 400 g and 600 g.

In order to determine the mechanical strength of the weld, the dynamometer testing method can be used.

Typically the width of the strip can be comprised between 0.5 and 3 cm and the quantity applied can be comprised between 10 and 30 g/m$^2$.

The geometry of the application of the heat-sealable adhesive makes it possible, when the support is folded, to produce very good-quality welds.

An embodiment of the invention relates to a peelable sterilization pack comprising a support as described previously comprising on one of its faces a heat-sealable adhesive, said adhesive forming a strip which describes a curve, said curve being symmetrical with respect to an axis, said axis being the axis of folding of the support, characterized in that the support is folded and partially heat-sealed such that the peelable pack has a heat-sealable opening intended to allow the items for sterilization to be positioned inside the pack. This peelable sterilization pack is particularly suitable for bulky and/or heavy objects, as the mechanical strength of the pack is increased because the pack is made in a single item. Moreover, as the pack has a fold, the load of the heavy objects is supported by the fold and not by the heat-sealed seam alone.

Another embodiment of the invention relates to a peelable sterilization pack comprising a support as described previously comprising on one of its faces a heat-sealable adhesive, said adhesive forming two strips which describe two curves, said curves being symmetrical to each other with respect to an axis, said axis being the axis of folding of the support, characterized in that the support is folded, trimmed and partially heat-sealed such that the peelable pack has a heat-sealable opening intended to allow the items for sterilization to be positioned inside the pack. The absence of a fold facilitates the opening of the packaging by the user.

An embodiment of the invention relates to a set of peelable packs comprising a first peelable pack as described previously, contained in a second pack as described previously, both packs being suited to the same sterilization method.

Typically the second pack can serve as transport packaging which can be removed just before entering a sterile room such as an operating theatre. Typically the second pack can be removed in the airlock, if there is one, which is before the sterile room. Thus the sterility of the external surface of the first pack is preserved for as long as possible.

According to a particular embodiment, the two packs are suitable for steam sterilization, the first pack is constituted by a nonwoven material which has a structure of SMS or SMMS type, the second pack is constituted by cellulose. The mechanical strength of the set of packs is provided mainly by the first pack constituted by a nonwoven material. The use of a second pack made of cellulose facilitates the evacuation of steam.

An embodiment of the present invention is a process for the production of a peelable pack as described previously comprising the following steps:
a) supplying a support suited to at least one sterilization method and to sterility maintenance;
b) applying a strip of heat-sealable adhesive onto one of the faces of the support such that the strip describes a curve, said curve being symmetrical with respect to an axis, said axis being the axis of folding of the support;
c) folding the support along said axis;
  partially heat-sealing the folded support such that the peelable pack obtained has a heat-sealable opening intended to allow the items for sterilization to be positioned inside the pack.

Another embodiment is a process for the production of a peelable sterilization pack as described previously comprising the following steps:

a) supplying a support suited to at least one sterilization method and to sterility maintenance;
b) applying two strips of heat-sealable adhesive onto one of the faces of the support such that the strips describe two curves, said curves being symmetrical to each other with respect to an axis, said axis being the axis of folding of the support;
c) folding the support along said axis;
d) trimming the support so as to remove the fold;
e) partially heat-sealing the folded support such that the peelable pack obtained has a heat-sealable opening intended to allow the items for sterilization to be positioned inside the pack, step e) is capable of being carried out before or simultaneously with step d).

An embodiment of the present invention is a process for the sterilization of a item comprising the following steps:

a) introducing the item to be sterilized into a peelable sterilization pack as described previously or into a set of peelable packs as described previously;
b) heat-sealing the pack or packs;
c) sterilizing the contents of the pack or set of packs.

Typically the items to be sterilized are medical devices arranged on an instrument tray.

A particular embodiment of the invention relates to a sterilization process as described previously, characterized in that the sterilization is a steam sterilization.

An embodiment of the invention relates to the use in a hospital environment of a pack as described previously or of a set of peelable packs as described previously.

An embodiment of the invention relates to a process for the production of a support as described previously comprising the following steps:

a) supplying a support suited to at least one sterilization method and to sterility maintenance;
b) applying a strip of heat-sealable adhesive onto one of the faces of the support such that the strip describes a curve, said curve being symmetrical with respect to an axis, or
b') applying two strips of heat-sealable adhesive to one of the faces of the support such that the strips describe two curves, said curves being symmetrical to each other with respect to an axis.

The support can have any shape or dimensions, the production method is suited to all desired pack dimensions.

The invention claimed is:

1. A support suited for at least one sterilization method and to maintain sterility, comprising:
   two faces;
   an axis of folding; and
   either (i) a first strip of heat-sealable adhesive on one of said faces, said first strip describing a first curve which is symmetrical to said axis, or (ii) a first strip of heat-sealable adhesive on one of said faces, said first strip describing a first curve, and a second strip of heat-sealable adhesive on said face, said second strip describing a second curve, said first and second curves are symmetrical to each other with respect to said axis, wherein
   said support when folded about said axis of folding forms an adhesive-adhesive contact between said first curve symmetrical to said axis or between said first curve and second curve symmetrical to each other and said axis so that said folded support is capable of being heat-sealed and constituting a peelable sterilization pack,
   said support is formed from a material which comprises a polymer selected from the group consisting of high density polyethylene, polypropylene, polyamide, polyester and mixtures thereof,
   said heat-sealable adhesive is an adhesive which has an adhesive-adhesive bond which is weaker than an adhesive-support bond, and
   said heat-sealable adhesive is a water-based adhesive which is applied to an area of the support coated with a hydrophobic agent.

2. The support according to claim 1, wherein said first curve is closed.

3. The support according to claim 1, wherein said material is suited for at least one sterilization method selected from the group consisting of steam sterilization, ethylene oxide sterilization and gas-plasma sterilization.

4. The support according to claim 3, said material is suited for at least two sterilization methods selected from the group consisting of steam sterilization, ethylene oxide sterilization and gas-plasma sterilization.

5. The support according to claim 3, wherein said material is suited for steam sterilization.

6. The support according to claim 1, wherein said material is nonwoven.

7. The support according to claim 1, wherein said material has an SMS or SMMS structure.

8. The support according to claim 1, wherein said first curve has a rectangular shape.

9. A peelable sterilization pack, comprising:
   a support comprising two faces, an axis of folding, and
   either (i) a first strip of heat-sealable adhesive on one of said faces describing a first curve which is symmetrical to said axis, or (ii) a first strip of heat-sealable adhesive on one of said faces, said first strip describing a first curve, and a second strip of heat-sealable adhesive on said face, said second strip describing a second curve, said first and second curves are symmetrical to each other with respect to said axis,
   said heat-sealable adhesive being an adhesive which has an adhesive-adhesive bond which is weaker than an adhesive-support bond, and said heat-sealable adhesive being a water-based adhesive which is applied to an area of the support coated with a hydrophobic agent,
   said support being folded along said axis to form an adhesive-adhesive contact between said first curve symmetrical to said axis or between said first curve and said second curve symmetrical to each other and said axis, and said first and eventually said second strip(s), and
   said adhesive-adhesive contact being partially heat-sealed to provide a heat-sealable opening,
   said heat-sealable opening allowing for positioning of items for sterilization inside said pack.

10. A process for producing a peelable sterilization pack, comprising the following steps:
    supplying a support suited to at least one sterilization method and to sterility maintenance, said support having two faces and an axis of folding;
    either (i) applying a strip of heat-sealable adhesive to one of said faces such that said strip describes a first curve, said first curve being symmetrical with respect to said axis, or (ii) applying two strips of heat-sealable adhesive on one of said faces such that said first strip describes a first curve, and a second strip describes a second curve, said first and second curves being symmetrical to each other with respect to said axis, said heat-sealable adhesive being an adhesive which has an adhesive-adhesive bond which is weaker than an adhesive-support bond, and said heat-sealable adhesive being a water-based adhesive which is applied to an area of the support coated with a hydrophobic agent;

folding the support along said axis to form an adhesive-adhesive contact between said first curve symmetrical to said axis or between said first curve and said second curve symmetrical to each other and said axis; and partially heat-sealing the folded support such that a peelable pack is obtained having a heat-sealable opening intended to allow the items for sterilization to be positioned inside the pack.

11. The process according to claim 10, wherein when said two strips of heat-sealable adhesive are applied on said face, and said folded support forms an adhesive-adhesive contact between said first curve and said second curve symmetrical to each other and said axis; and said folded support is trimmed to remove the fold before or simultaneously with partially heat sealing.

12. A method for the sterilization of a item comprising the following steps:

introducing an item to be sterilized into a peelable sterilization pack according to claim 9;

heat-sealing the pack; and sterilizing the contents of the pack.

13. The method according to claim 12, wherein the sterilization is a steam sterilization.

14. The method of according to claim 12, wherein said item is a medical device.

15. A method for producing a support, comprising the following steps:

supplying a support having two faces suited to at least one sterilization method and to sterility maintenance;

either (i) applying at least one strip of heat-sealable adhesive to one of said faces such that said at least one strip describes a curve, said curve being symmetrical with respect to an axis, or (ii) applying two strips of heat-sealable adhesive on one of said faces such that said first strip describes a first curve, and a second strip describes a second curve, said first and second curves being symmetrical to each other with respect to said axis, said heat-sealable adhesive being an adhesive which has an adhesive-adhesive bond which is weaker than an adhesive-support bond, and said heat-sealable adhesive being a water-based adhesive which is applied to an area of the support coated with a hydrophobic agent.

16. A kit of peelable sterilization packs, comprising:

a first sterilization pack according to claim 9, a second sterilization pack, wherein said first sterilization pack is contained inside said second sterilization pack, and said first and second sterilization pack have a support formed from a material which is suited for the same sterilization method.

17. The kit of peelable sterilization packs, according to claim 16, said second sterilization pack comprising:

a support comprising two faces, an axis of folding, and either (i) a first strip of heat-sealable adhesive on one of said faces describing a first curve which is symmetrical to said axis, or (ii) a first strip of heat-sealable adhesive on one of said faces, said first strip describing a first curve, and a second strip of heat-sealable adhesive on said face, said second strip describing a second curve, said first and second curves are symmetrical to each other with respect to said axis, said heat-sealable adhesive being an adhesive which has an adhesive-adhesive bond which is weaker than an adhesive-support bond, and said heat-sealable adhesive being a water-based adhesive which is applied to an area of the support coated with a hydrophobic agent, said support being folded along said axis to form an adhesive-adhesive contact between said first curve symmetrical to said axis or between said first curve and said second curve symmetrical to each other and said axis, and said first and eventually said second strip(s), and said adhesive-adhesive contact being partially heat-sealed to provide a heat-sealable opening, said heat-sealable opening allowing for positioning of items for sterilization inside said pack.

18. The kit of peelable sterilization packs, according to claim 16, wherein said first pack is formed from a nonwoven material which has an SMS or SMMS structure, and said second pack is constituted by cellulose.

* * * * *